United States Patent
Abkai et al.

(10) Patent No.: US 10,165,991 B2
(45) Date of Patent: Jan. 1, 2019

(54) ORTHODONTIC DIAGNOSTIC METHOD

(71) Applicant: SIRONA DENTAL SYSTEMS GMBH, Bensheim (DE)

(72) Inventors: Ciamak Abkai, Heddesheim (DE); Kai Lindenberg, Wersau (DE); Björn Ludwig, Traben-Trarbach (DE)

(73) Assignee: DENTSPLY SIRONA Inc., York, PA (US)

( * ) Notice: Subject to any disclaimer, the term of this patent is extended or adjusted under 35 U.S.C. 154(b) by 119 days.

(21) Appl. No.: 15/529,529

(22) PCT Filed: Nov. 25, 2015

(86) PCT No.: PCT/EP2015/077594
§ 371 (c)(1),
(2) Date: May 25, 2017

(87) PCT Pub. No.: WO2016/083431
PCT Pub. Date: Jun. 2, 2016

(65) Prior Publication Data
US 2017/0303877 A1    Oct. 26, 2017

(30) Foreign Application Priority Data
Nov. 25, 2014  (DE) ......................... 10 2014 223 967

(51) Int. Cl.
*A61B 6/00* (2006.01)
*A61C 7/00* (2006.01)
*A61B 6/14* (2006.01)

(52) U.S. Cl.
CPC ............... *A61B 6/145* (2013.01); *A61B 6/14* (2013.01); *A61B 6/40* (2013.01); *A61B 6/463* (2013.01); *A61B 6/466* (2013.01); *A61B 6/5235* (2013.01); *A61C 7/002* (2013.01); *A61B 6/5247* (2013.01)

(58) Field of Classification Search
CPC .................................... A61B 6/00; A61C 7/00
USPC ......................................................... 382/128
See application file for complete search history.

(56) References Cited

U.S. PATENT DOCUMENTS

| | | | |
|---|---|---|---|
| 9,579,170 B2 * | 2/2017 | Van Lierde et al. | |
| 9,675,305 B2 * | 6/2017 | Bergersen | |
| 2003/0169913 A1 | 9/2003 | Kopelman | |
| 2007/0258638 A1 | 11/2007 | Howerton, Jr. | |
| 2012/0063564 A1 | 3/2012 | Klingenbeck | |

FOREIGN PATENT DOCUMENTS

| | | |
|---|---|---|
| DE | 102011080700 A1 | 2/2013 |
| DE | 102010002206 A1 | 5/2014 |
| DE | 102012221374 A1 | 5/2014 |
| EP | 2165672 A2 | 3/2010 |

\* cited by examiner

*Primary Examiner* — Abolfazl Tabatabai
(74) *Attorney, Agent, or Firm* — Dentsply Sirona Inc.

(57) ABSTRACT

The invention relates to an orthodontic diagnostic method wherein at least one initial two-dimensional X-ray image (1) of a first zone (2) of a head (3) is taken. Then at least one three-dimensional X-ray image (4) of a second zone (5) of a dental situation is taken, and the three-dimensional X-ray image (4) is combined with the initial two-dimensional X-ray image (1) using a registration process in order to obtain a full image (8).

10 Claims, 2 Drawing Sheets

ORTHODONTIC DIAGNOSTIC METHOD

TECHNICAL FIELD

The invention relates to an orthodontic diagnostic method, wherein at least one initial two-dimensional x-ray image of a head is taken.

PRIOR ART

Several orthodontic diagnostic methods are known from the prior art.

In a cephalometric analysis, a lateral cephalometric x-ray exposure is made, and characteristic structures in this cephalometric x-ray image are measured. Different orthodontic measurement values are thereby determined, e.g., a Frankfurt horizontal, a distance between the chin and the temporomandibular joint, or a distance between the base of the skull and the temporomandibular joint.

One disadvantage of this method is that the orthodontic measurement values are measured manually in the lateral cephalometric x-ray image, consuming a large amount of time.

With an ongoing diagnostic, multiple cephalometric x-ray images are made at regular time intervals, wherein the significant orthodontic measurement values are measured in each of the two-dimensional cephalometric x-ray images, and the time-dependent variation in these measurement values may be assessed depending upon the treatment.

An additional disadvantage of classical cephalometric analysis is that the measured orthodontic measurement values are dependent upon the positioning and alignment of the patient's head. An incorrect positioning of the patient's head may thus lead to measurement errors.

The object of the entire invention is thus to provide an orthodontic diagnostic method that enables a certain, error-free, and time-saving analysis and determination of the orthodontic measurement values.

DESCRIPTION OF THE INVENTION

The invention relates to an orthodontic diagnostic method, wherein at least one initial two-dimensional x-ray image of a first zone of a head is taken. Then, at least one three-dimensional x-ray image of a second zone of a dental situation is taken, wherein the three-dimensional x-ray image is combined with the initial two-dimensional x-ray image by means of a registration process in order to obtain a full image.

The initial two-dimensional x-ray image may be a lateral cephalometric two-dimensional x-ray image that records at least a partial zone of the head of a patient. For example, the recorded first zone may include characteristic fixed points such as the temporomandibular joint or characteristic points of the base of the skull. The known fixed points may then be used for a comparative superposition in the registration. The three-dimensional x-ray image may be a DVT image which records the second zone that, for example, includes the mandible. In addition to the first three-dimensional x-ray image, additional three-dimensional x-ray images may also be taken at regular time intervals, in order to implement an ongoing diagnostic. The registration method may take place automatically by means of a computer, wherein the two-dimensional x-ray image is combined with the three-dimensional x-ray image. Characteristic structures may thereby be used in the two images, such as a characteristic shape of the mandible, the shape of the maxilla, the temporomandibular joint, or the chin. In the registration method, an optimization algorithm may be used that applies the method of least squares, wherein the—normally transitory and rotational—parameters to be optimized are modified step by step in order to arrive at an optimal solution. To accelerate this optimization algorithm, the search space may be reduced, wherein information about the positioning of the head relative to the x-ray device used may be considered.

One advantage of this method is that only a small second zone of the dental situation is recorded for the diagnostic, wherein the three-dimensional x-ray image is registered with the initial two-dimensional x-ray image of a markedly larger zone of the head. For a series of three-dimensional x-ray images, each of the three-dimensional x-ray images is registered with the same initial two-dimensional x-ray image. The total dose is thereby minimized in comparison to a series of three-dimensional x-ray images of the entire head.

An additional advantage of the method is that, in comparison to the classical cephalometric analysis, an incorrect positioning of the patient is unproblematic, since the distances between relevant measurement points in the three-dimensional x-ray image remain unchanged in comparison to a projected two-dimensional image. In case of a slight rotation of the patient's head, the projection of the patient's head onto the two-dimensional x-ray image, and, therefore, also the distances between the relevant measurement points, are altered.

An additional advantage of this method is that the orthodontic measurement values may be determined automatically by means of a computer using the combined complete image. In comparison to manual measurement in classical cephalometric analysis, the time requirement is thus reduced, and possible errors arising from manual measurement are prevented.

Multiple three-dimensional x-ray images of the second zone of the dental situation may advantageously be taken in succession, at regular time intervals.

An ongoing diagnostic as a function of time is thereby enabled. With certain orthodontic treatments, the healing process or the progression of a dental correction by means of a dental brace may thereby be checked.

The initial two-dimensional x-ray image may, advantageously, be a lateral cephalometric image.

The lateral cephalometric image thus includes the larger first zone that includes the base of the skull, the temporomandibular joint, the chin, the maxilla, and the mandible.

The three-dimensional x-ray image may, advantageously, be a DVT image.

The DVT image thus contains a smaller zone that, for example, includes the mandible, the maxilla, or also a group of teeth.

The second zone may, advantageously, be a maxilla and/or of a mandible.

The entire dental situation is thereby measured.

The first zone of the head may, advantageously, include the second zone of the dental situation, wherein the first zone of the head includes specific fixed points such as a point at the base of the skull or a temporomandibular joint.

The fixed points are thus anatomically stable structures that remain unchanged relative to the skull and may thereby serve as reference points in the measurement of specific, characteristic distances or orthodontic measurement values.

Advantageously, at least one orthopedic measurement value of a jaw, a tooth, and/or multiple teeth may be determined relative to a fixed point.

With a dental correction, the chronological position change of an individual tooth or of multiple teeth may thereby be determined and shown relative to the skull. This ongoing diagnostic then enables the treating physician to adapt the orthodontic treatment.

A segmentation and/or a classification of orthodontic structures (such as a maxilla, a mandible, a base of the skull, a palatal area, or a temporomandibular joint) may, advantageously, be implemented automatically by means of a computer, in order to determine the orthopedic measurement value using the combined complete image.

Via the segmentation, the cited structures are thus automatically demarcated relative to their surrounding tissue and are subsequently classified using their characteristic shape. The segmented characteristic structures may also be highlighted with color in the graphical presentation.

The segmented orthodontic structures, which are present in both the two-dimensional x-ray image and in the three-dimensional x-ray image, may be used for registration, in that these structures are superimposed on both x-ray images to be registered.

The segmentation may also take place partially automatically, wherein the user manually selects one or several points on a boundary of the structure, and the entire segmentation of this structure subsequently proceeds automatically by means of the computer, taking into consideration the selected points.

A chronological progression of a segmented orthodontic structure may, advantageously, be determined using the successively acquired three-dimensional x-ray images.

An ongoing diagnostic may thereby be implemented for a specific orthodontic structure, such as the maxilla, the mandible, an individual tooth, or also a group of teeth.

For the ongoing diagnostic, the progression of the orthodontic structure may, advantageously, be graphically presented as a function of time.

The graphical presentation of the ongoing diagnostic thereby enables the treating physician to assess the course of treatment and to adapt the treatment if necessary.

The registration between the initial two-dimensional x-ray image and the at least one three-dimensional x-ray image may, advantageously, take place using known geometric dimensions of an x-ray device that is used, wherein a perspective distortion of a recorded object in the two-dimensional x-ray image is taken into consideration.

With the lateral cephalometric image, the perspective distortion may be determined using the known geometric values of the x-ray device. These values are the distance between the sensor and the object (such as the patient's head), the distance between the object and the x-ray source, the setting of the actuators, and the setting of the diaphragms. An optimization algorithm may be applied in the registration, wherein known tolerances of the mechanical elements (such as the actuators and the diaphragms) strongly limit the parameter space of a search space.

In the registration between the initial two-dimensional x-ray image and the at least one three-dimensional x-ray image, a known position and/or alignment of an object to be recorded (such as a mandible and/or a maxilla) relative to an x-ray device to be recorded may is advantageously used.

The positioning of the patient, and therefore of the subject to be recorded, is thus taken into account in the registration. The position and the alignment of the patient's head may be adjusted at the x-ray device using specific positioning means, such as a face support and a chin rest. The information about the position and the alignment of the patient's head thus markedly reduces the solution space, with the application of the optimization algorithm.

The known position and/or the known alignment of the object to be recorded relative to the x-ray device may, advantageously, be taken into account in the initiation of a search space and/or of a starting solution in an optimization algorithm.

The calculation time for the registration is thereby reduced, and possible registration errors are prevented. A starting solution for the optimization algorithm may thus be selected precisely, to within a few centimeters, in comparison to the actual position and alignment of the patient's head. The reduced search space leads to the situation that the risk of landing in a false local minimum is reduced after the run of the automated optimization algorithm.

BRIEF DESCRIPTION OF THE DRAWINGS

The invention is explained using the drawings. Shown are
FIG. 1 a sketch for clarifying the present method with a combined complete image.

EXEMPLARY EMBODIMENTS

Figure 1:
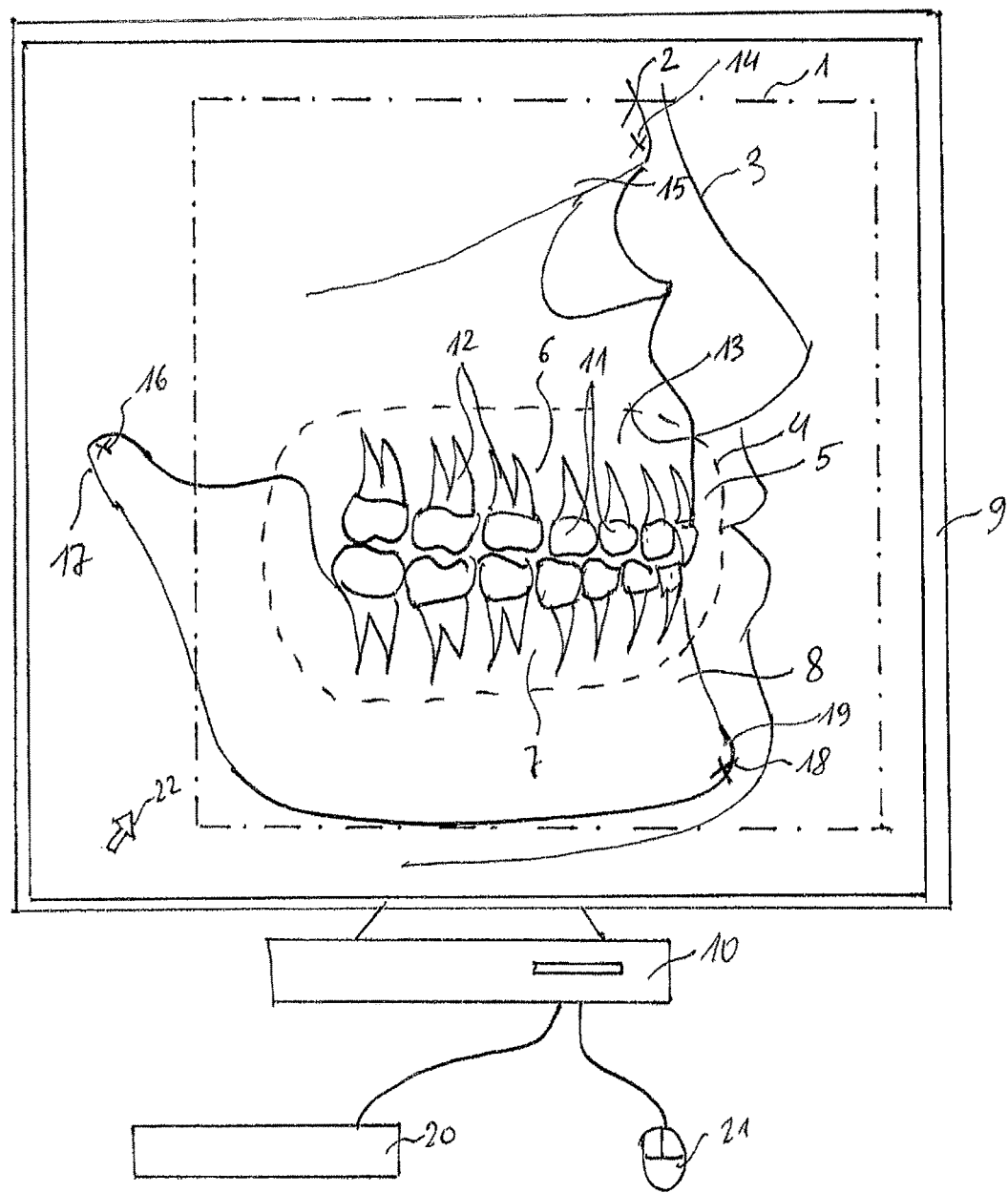

FIG. 1 shows a sketch illustrating the present orthodontic diagnostic method. In a first method step, an initial two-dimensional x-ray image 1 of a first zone 2 is taken, wherein the first zone 2 at least partially includes a head 3 of a patient. In the present case, the two-dimensional x-ray image is a lateral cephalometric x-ray image. Subsequently, at least one three-dimensional x-ray image 4 of a second zone 5 (shown with dashed lines) is taken, wherein the second zone 5 in the following instance includes a maxilla 6 and a mandible 7. The boundary of the first zone 2 is represented by a dash-dot line. In a further method step, using a registration method, the two-dimensional x-ray image 1 is combined with the three-dimensional x-ray image 4 to form a complete image 8. The combined complete image 8 is graphically displayed by means of display device 9, such as a monitor. The combination of the initial two-dimensional x-ray image 1 and the three-dimensional x-ray image 4 takes place by means of a computer 10, wherein an optimization algorithm is applied. Characteristic structures, the individual teeth 11, dental roots 12, or characteristic curves of a jawbone 13 are thereby superimposed in the two x-ray images 1 and 4. For example, the optimization algorithm may be based upon a method of least squares.

In addition to the first three-dimensional x-ray image 4, additional three-dimensional x-ray images of the zone 5 may also be taken at regular time intervals, so that an ongoing diagnostic is enabled. For example, the changes in the position and alignment of the teeth 11, as well as of the dental roots 12, may thereby be implemented by means of a dental brace in a dental correction treatment. The first zone 2 may include specific fixed points: the one first fixed point 14 at the face side of the base of the skull 15 and a second fixed point 16 at the temporomandibular joint 17. Using the combined complete image 8, specific orthodontic distances may be determined, e.g., a distance between the second fixed point 16 at the temporomandibular joint 17 and a tip 18 of the chin 19. Using the complete image 8, the position and the alignment of the individual teeth 11 and the dental roots 12 may also be determined relative to the fixed points 14 and 16. Conventional means of operation, such as a keyboard 20 and a mouse 21, are connected to the computer 10, so that the user may select specific zones or structures in the complete image 8 by means of a cursor 22. The selected structure may be highlighted in color. The determination of the orthodontic distances or measurement values may take place automatically by means of the computer 10, wherein a segmentation and/or a classification of the orthodontic structures, such as the maxilla 6, the mandible 7, the base of the skull 15, or the temporomandibular joint 17, may also take place automatically. The result of the automatic method may thus be a table with the significant orthodontic measurement values.

Figure 2:
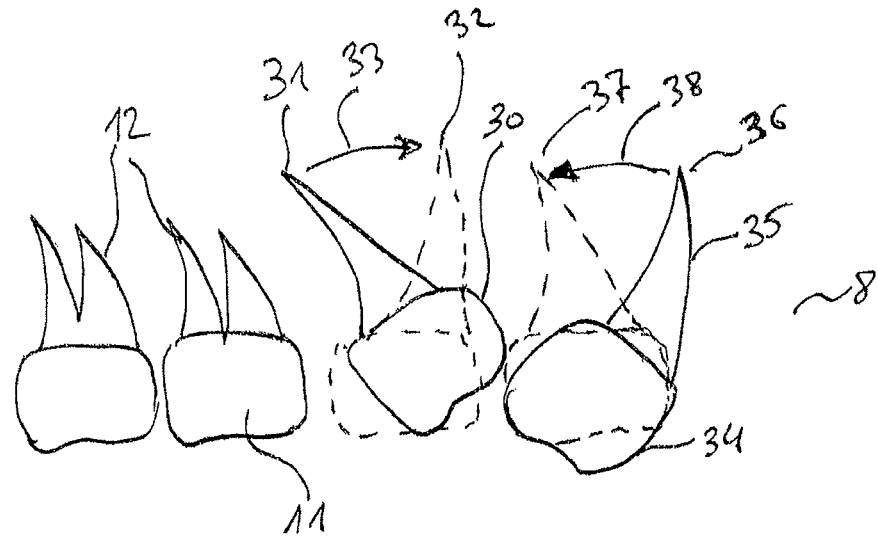
FIG. 2 a sketch of a time-dependent progression of the teeth and the dental root in a dental correction.

FIG. 2 shows a drawing of the teeth 11 and the dental roots 12 for a dental correction. In the course of the dental correction treatment, a first tooth 30 having a first dental root 31 is brought from an initial position into a final position 32 (shown with a dashed line), wherein the position change is indicated by the arrow 33. A second tooth 34 having a second dental root 35 is brought from an initial position 36 into a final position 37 (shown with a dashed line) at the end of the dental correction treatment, wherein the position change is indicated by an arrow 38. The second tooth 34 and the second dental root are thus imaged in the initial position 36 in a first three-dimensional x-ray image of an image series at the start of the dental correction treatment, and the final position 37 is imaged in a last three-dimensional image at the end of this image series. The course of the position change can thus be graphically tracked as a function of time.

Figure 3:
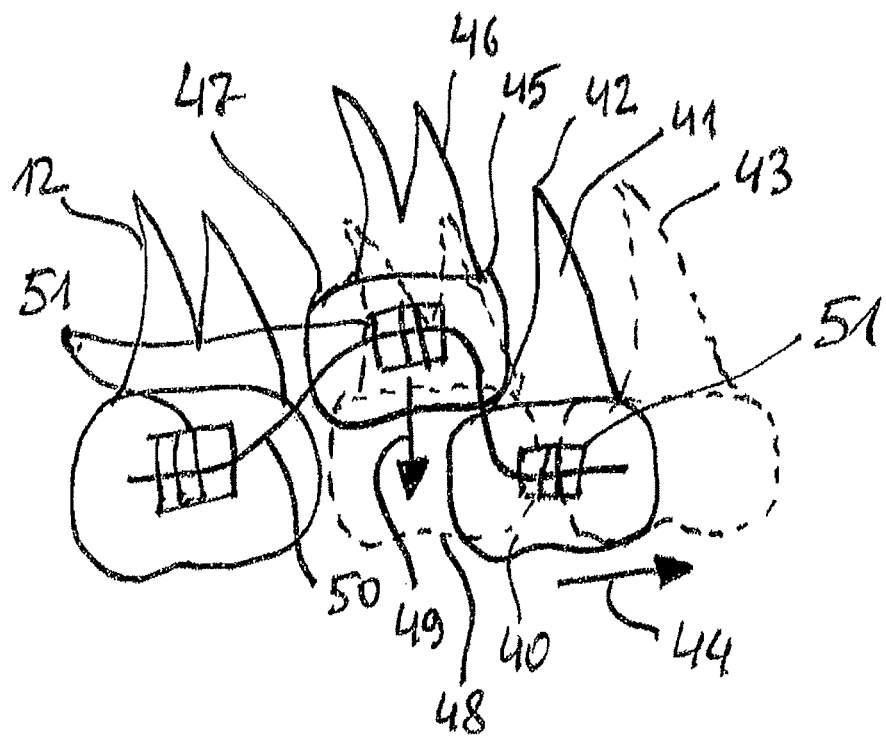
FIG. 3 a sketch of a time-dependent progression of the teeth and the dental root in an alternative dental correction.

FIG. 3 shows a drawing of the teeth 11 and the dental roots 12, wherein a third tooth 40 having a third dental root 41 is brought from an initial position 42 (shown with a solid line) into a final position 43 (shown with a dashed line) by means of a dental brace during the dental correction treatment, wherein the position change is indicated by the arrow 44. Moreover, a fourth tooth 45 having a fourth dental root 46 is moved from an initial position 47 into a final position 48 after the dental correction, which is shown with a dashed line. The position change of the fourth tooth 45 is there indicated by the arrow 49. The position change or correction of the individual teeth 11, 40, and 45 may thereby take place by means of a dental brace 50 with the brackets 51 attached to the teeth.

REFERENCE CHARACTERS

1 Initial two-dimensional x-ray image
2 first zone
3 head
4 three-dimensional x-ray image
5 second zone
6 maxilla
7 mandible
8 complete image
9 display device
10 computer
11 teeth
12 dental root
13 jawbone
14 first fixed point
15 base of the skull
16 second fixed point
17 temporomandibular joint
18 tip
19 chin
20 keyboard
21 mouse
22 cursor
30 first tooth
31 first dental root
32 final position
33 Arrow
34 second tooth
35 second dental root
36 initial position
37 final position
38 Arrow
40 third tooth
42 initial position
43 final position
44 Arrow
45 fourth tooth
46 fourth dental root
47 initial position
48 final position
49 position change
50 dental brace
51 brackets

The invention claimed is:

1. An orthodontic diagnostic method, the method comprising taking at least one initial two-dimensional x-ray image of a first zone of a head,
 then taking at least one three-dimensional x-ray image of a second zone of a dental situation, wherein the three-dimensional x-ray image is combined with the initial two-dimensional x-ray image by a registration method to form a complete image (8),
 wherein, for an ongoing diagnostic, multiple three-dimensional x-ray images of the second zone of the dental situation are taken in succession at regular time intervals,
 wherein the first zone of the head comprises the second zone of the dental situation,
 wherein the first zone of the head includes defined fixed points, the defined fixed point is a point at the base of the skull or a temporomandibular joint, and
 wherein the initial two-dimensional x-ray image is a lateral cephalometric image.

2. The orthodontic diagnostic method according to claim 1, wherein the three-dimensional x-ray image is a DVT image.

3. The orthodontic diagnostic method according to claim 1, wherein the second zone comprises a maxilla and/or a mandible.

4. The orthodontic diagnostic method according to claim 1, wherein, for the ongoing diagnostic diagnostic, at least one orthopedic measurement value of a jaw, a tooth, and/or multiple teeth is determined relative to a fixed point.

5. The orthodontic diagnostic method according to claim 4, wherein a segmentation and/or a classification of orthodontic structures a is implemented automatically by a computer, in order to determine the orthopedic measurement value using the combined complete image, wherein the orthodontic structures are a maxilla, a mandible, a base of the skull, or a temporomandibular joint.

6. The orthodontic diagnostic method according to claim 5, wherein a chronological progression of a segmented orthodontic structure is determined using the successively acquired three-dimensional x-ray images.

7. The orthodontic diagnostic method according to claim 6, wherein, for the ongoing diagnostic, the chronological progression of the orthodontic structure may be graphically presented as a function of time.

8. The orthodontic diagnostic method according to claim 1, wherein the registration between the initial two-dimensional x-ray image and the at least one three-dimensional x-ray image is implemented using known geometric dimensions of an employed x-ray device, wherein a perspectival distortion of a recorded subject in the two-dimensional x-ray image is taken into consideration.

9. The orthodontic diagnostic method according to claim 1, wherein a known position and/or alignment of an object to be recorded relative to an x-ray device is used in the registration between the initial two-dimensional x-ray image and the at least one three-dimensional x-ray image-, wherein the object to be recorded is a mandible and/or a maxilla.

10. The orthodontic diagnostic method according to claim 9, wherein the known position and/or alignment of the object to be recorded relative to the x-ray device are taken into account in the initiation of a search space and/or of a starting solution in an optimization algorithm.

\* \* \* \* \*